US00PP27491P2

(12) United States Plant Patent
Probst

(10) Patent No.: US PP27,491 P2
(45) Date of Patent: Dec. 20, 2016

(54) ***COREOPSIS* PLANT NAMED 'POLARIS'**

(50) Latin Name: ***Coreopsis* hybrid**
Varietal Denomination: Polaris

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 243 days.

(21) Appl. No.: 14/120,963

(22) Filed: Jul. 16, 2014

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

Green Leaf Plants Perennials & Herbs 2013/2014 retrieved on May 9, 2016, retrieved from the Internet at <http://www.glplants.com/system/cms/files/files/000/000/026/original/Green_Leaf_Perennial_Catalog.pdf> pp. 1-7, 18 and 60.*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Polaris' that is characterized its compact plant habit reaching 37.5 to 45 cm in height and an average of 37.5 cm in spread, its prolific blooming habit from mid June until frost in Connecticut, its large inflorescences with ray florets that are are solid white in color with no eye zone (even under cool growing conditions), its relatively sterile inflorescences when grown under typical garden conditions that do not require deadheading of spent blooms for continuous bloom, and its reliably perennial habit in U.S.D.A. Zone 5.

2 Drawing Sheets

Botanical classification: *Coreopsis* hybrid.
Variety denomination: 'Polaris'.

BACKGROUND OF THE INVENTION

The present invention relates to a new and distinct cultivar of *Coreopsis* plant, botanically of hybrid origin and known as *Coreopsis* 'Polaris' and will be referred to hereinafter by its cultivar name, 'Polaris'. The new cultivar of *Coreopsis* is an herbaceous perennial grown for landscape and container use.

The new Invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms.

The Inventor made a controlled cross in July of 2009 in his test garden in Hubbardston, Mass. between an unnamed plant from his breeding program, ref. no. T 09-1, as the female parent and pollen that was pooled from a variety of unnamed plants from his breeding program as the male parent (all nearly sterile). The exact characteristics of the pollen parent are therefore unknown. 'Polaris' was selected in October of 2010 as a single unique plant amongst the resulting seedlings.

Asexual propagation of the new cultivar was first accomplished by stem cuttings under the direction of the Inventor in Kensington, Conn. in October of 2010. Asexual propagation by stem cutting has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Polaris' as a unique cultivar of *Coreopsis*.

1. 'Polaris' exhibits a compact plant habit reaching 37.5 to 45 cm in height and an average of 37.5 cm in spread.
2. 'Polaris' exhibits a prolific blooming habit from mid June until frost in Connecticut.
3. 'Polaris' exhibits large inflorescences with ray florets that are are solid white in color with no eye zone (even under cool growing conditions).
4. 'Polaris' is relatively sterile when grown under typical garden conditions and does not require deadheading of spent blooms for continuous bloom.
5. 'Polaris' is reliably perennial in U.S.D.A. Zone 5.

The female parent of 'Polaris', Ref. No. T 09-1, differs from 'Polaris' in being highly fertile and produces full seed heads that result in a one month blooming period without deadheading. 'Polaris' can be most closely compared to *Coreopsis* cultivars 'Star Cluster' (U.S. Plant Pat. No. 23,035) and 'Snowberry' (U.S. Plant Pat. No. 18,560). 'Star Cluster' is similar to 'Polaris' in having inflorescences with white ray florets and in being reletively sterile and disease resistant. 'Star Cluster' differs from 'Polaris' in being taller in height and in having inflorescences with ray florets that are white in color with a small purple eye zone with the ray florets becoming suffused with purple under cool growing conditions. 'Snowberry' is similar to 'Polaris' in having inflorescences with whitish colored ray florets. 'Snowberry' differs from 'Polaris' in having inflorescences with ray florets that are light primrose yellow in color with a maroon eye and in being less reliably perennial in U.S.D.A. Zone 5.

BRIEF DESCRIPTION OF THE DRAWINGS

The accompanying colored photographs illustrate the overall appearance and distinct characteristics of the new *Coreopsis*.

The photograph in FIG. 1 was taken in late June of a 10 month-old plant of 'Polaris' as grown outdoors in a one gallon container in Kensington, Conn. and shows the plant habit in bloom.

Figure 1:
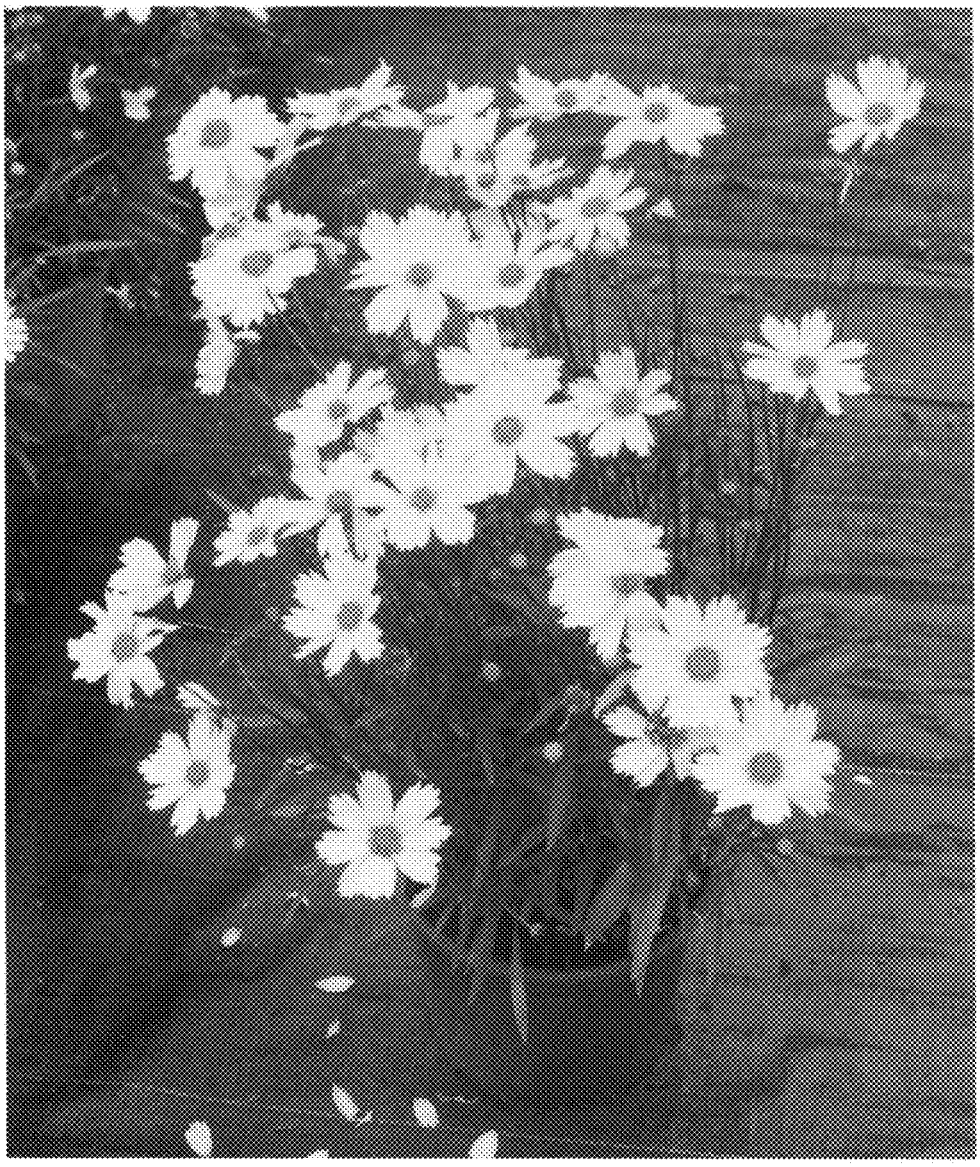
Figure 2:
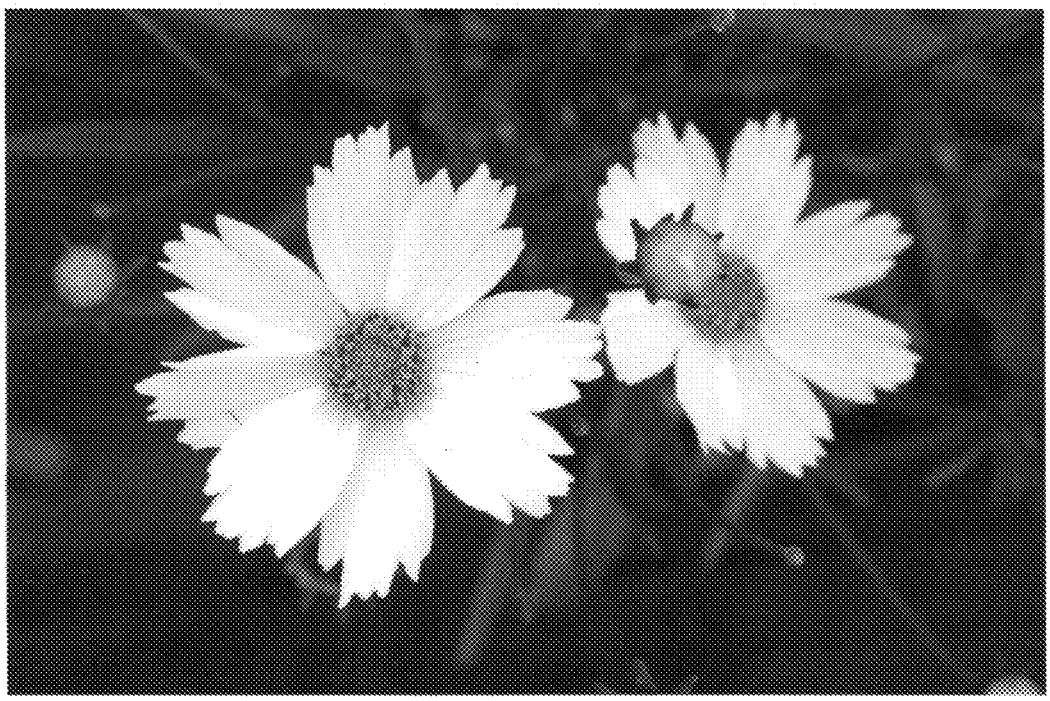

The photograph in FIG. 2 was taken in early September of a 6 month-old plant of 'Polaris' as grown outdoors in a one gallon container in Kensington, Conn. and provides a close-up view of the inflorescences.

The colors in the photographs are as close as possible with the photographic and printing technology utilized. The color values cited in the detailed botanical description accurately describe the colors of the new *Coreopsis*.

DETAILED BOTANICAL DESCRIPTION

The following is a detailed description of the new cultivar as observed for four years in a test garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period*.—Blooms from mid June until frost in central Massachusetts.

*Plant habit*.—Herbaceous perennial, clump-forming, compact, upright leafy flowering stems with inflorescences held above the foliage.

*Height and spread*.—Reaches 37.5 to 45 cm in height and an average of 37.5 cm in spread.

*Cold hardiness*.—At least to U.S.D.A Zone 5.

*Diseases resistance*.—More resistance to powdery mildew has been observed in comparison to *Coreopsis grandiflora* cultivars grown under the same conditions.

*Root description*.—Fibrous, fine and well-branched.

*Propagation*.—Terminal stem cuttings and division.

*Growth rate*.—Vigorous but stays compact.

Stem description:

*Shape*.—Tetragonal, solid.

*Stem color*.—144A with mature stems flecked with 165A.

*Stem size*.—Main stem averages 9 cm in length with laterals an average of 5 cm in length (excluding peduncles), average of 3 mm in width.

*Stem surface*.—Glabrous when young, ridged and sparsely covered with translucent hairs up to 1 mm in length when mature.

*Branching habit*.—Freely branched, typically branched as opposite laterals at each node, average of 3 branches per main stem, branch internode about 3.5 cm in length.

Foliage description:

*Leaf division*.—Simple.

*Leaf margins*.—Entire to bifid.

*Leaf size*.—Average of 6.5 cm in length and 3 cm in width when bifid and an average of 6.5 cm in length and 6 mm in width when entire.

*Leaf shape*.—Lanceolate.

*Leaf base*.—Cuneate.

*Leaf apex*.—Acute.

*Leaf venation*.—Only midrib is visible, not conspicuous, same coloration as leaf.

*Leaf attachment*.—Sessile.

*Leaf arrangement*.—Opposite.

*Leaf surface*.—Lower surface smooth and dull, upper surface slightly glossy and very sparsely covered with short stiff transluscent hairs to small to measure.

*Leaf color*.—Young and mature; upper surface a blend of 137A and 139A, lower surface 137C.

Flower description:

*Inflorescence type*.—Campitulum with ray florets surrounding disk florets in the center, forming a radiant head, inflorescences are borne on terminals arising from leaf axils, in loose open clusters.

*Lastingness of inflorescence*.—About one week until senescence of ray flowers, bracts and disk flowers are persistent.

*Fragrance*.—Slightly fragrant.

*Quantity of inflorescences*.—Very free flowering, over 200 inflorecenses on a six month-old plant.

*Inflorescence size*.—Average 3 cm in depth and up to 6.3 cm in diameter with disk portion up to 1.25 cm in diameter.

*Inflorescence buds*.—Average of 1 cm in depth and diameter, shape is spherical, color is a color between 18A and 11A.

*Peduncle*.—Strong, average of 9 cm in length and 1 mm in diameter, 144A in color, shiny surface.

Involucral bracts:

*Bract number*.—Two rows of 8.

*Bract arrangement*.—Outer bracts are unfused and held at about a 45° angle when flower is fully open becoming horizontal to downward after ray florets drop, inner bracts overlap and surround receptacle with apical portion spreading (campanulate-like).

*Bract size*.—Outer bracts about 8 mm in length and 2 mm in width, inner bracts about 1 cm in length and 5 mm in width.

*Bract color*.—Outer bracts, both surfaces; 144A at the base, 137A at the tips, inner bracts; base is 137A with a blend of 165A, tip is a blend of 154B and 137A.

*Bract texture*.—Outer bracts glabrous on both surfaces, inner bracts waxy on both surfaces.

*Bract apex*.—Acute.

*Bract base*.—Truncate.

*Bract shape*.—Outer bracts lanceolate, inner bracts broadly lanceolate.

Ray florets (sterile):

*Number*.—8.

*Shape*.—Obovate, appearance of three longitudinal sections.

*Size*.—Up to 3 cm in length and 1.9 cm in width.

*Apex*.—Three-lobed with 0-4 irregular lobules per lobe.

*Base*.—Broadly cuneate.

*Margins*.—Entire on sides, notched on apex.

*Aspect*.—Held flat, perpendicular to peduncle.

*Texture*.—Glabrous on both surfaces.

*Color*.—Upper and lower surface when opening and when fully open; NN155A.

Disk florets (male and female):

*Number*.—An average of 80.

*Shape*.—Tubular, corolla is fused, flared at apex.

*Size*.—About 6 mm in length and 2 mm in width.

*Color*.—In masse; 17A, corolla; base (tube) is 9B in color, flared portion is 17A.

*Receptacle*.—About 8 mm in diameter and 3 mm in depth, N144A in color.

Reproductive organs:

*Presence*.—Disk flowers are perfect, ray flowers sterile.

*Gynoecium*.—1 Pistil, 5 mm in length, style is very fine and 11C in color, bifid pillose stigma is 16A in color with branches about 1 mm in length and recurved, ovary is 2 mm in length, 1 mm in width, placement is inferior, translucent and 150D in color.

*Androcoecium*.—5 stamens, fused into tube surrounding style, 3 mm in length and 0.7 mm in width, about 166A in color, no pollen was observed.

*Fruit*.—No fruit development was observed, relatively sterile.

It is claimed:

1. A new and distinct cultivar of *Coreopsis* plant named 'Polaris' as herein illustrated and described.

* * * * *